(12) United States Patent
Bergren

(10) Patent No.: US 6,559,305 B1
(45) Date of Patent: May 6, 2003

(54) LINEZOLID—CRYSTAL FORM II

(75) Inventor: Michael S. Bergren, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/154,359

(22) Filed: May 23, 2002

Related U.S. Application Data

(62) Division of application No. 09/772,239, filed on Jan. 29, 2001, now Pat. No. 6,444,813.
(60) Provisional application No. 60/179,837, filed on Feb. 2, 2000.

(51) Int. Cl.⁷ .............................................. C07D 413/10
(52) U.S. Cl. ...................................................... 544/137
(58) Field of Search .......................................... 544/137

(56) References Cited

U.S. PATENT DOCUMENTS

| | | | |
|---|---|---|---|
| 5,688,792 A | 11/1997 | Barbachyn et al. ...... | 514/235.5 |
| 5,837,870 A | 11/1998 | Pearlman et al. ........... | 544/137 |

FOREIGN PATENT DOCUMENTS

| | | | |
|---|---|---|---|
| WO | WO97/37980 | 10/1997 | ......... C07D/263/24 |
| WO | WO99/24393 | 5/1999 | ......... C07C/233/16 |

OTHER PUBLICATIONS

J. Med. Chen., vol. 39, 1996, pp. 673–679, XP002168553.
"Linezolid. Oxazolidinone Antibacterial" Drugs of the Future, es, barcelona, vol. 21, No. 11, 1996, pp. 1116–1123 XP000654643.
Tetrahedron Letters, 40(26), 4855 (1999).
Zurenko G E Et Al, Oxazolidinone antibacterial agents: development of the clinical candidates eperezolid and linezolid candidates eperezolid and linezolid Expert opinion on Investigational Drugs, GB, Ashley Pub. Ltd. London, vol. 6, No. 2, 1997, pp. 151–158 XP000654528.

*Primary Examiner*—Robert W. Ramsuer
(74) *Attorney, Agent, or Firm*—John H. Engelmann

(57) ABSTRACT

The invention is a novel crystal form (Form II) of a known compound, linezolid

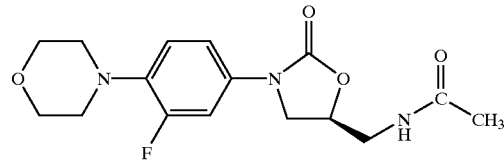

which is useful as an antibacterial agent.

2 Claims, No Drawings

LINEZOLID— CRYSTAL FORM II

CROSS-REFERENCE TO RELATED APPLICATIONS

This application is a divisional of U.S. patent application Ser. No. 09/772,239, filed Jan. 29, 2001 now U.S. Pat. No. 6,444,813 and claims the benefit of the following provisional application: U.S. Ser. No. 60/179,837, filed Feb. 2, 2000, under 35 USC §119(e)(i).

BACKGROUND OF THE INVENTION

1. Field of the Invention

The field of the invention is a novel crystal form of a known compound, linezolid which is pharmaceutically useful as an antibacterial agent.

2. Description of the Related Art

U.S. Pat. No. 5,688,792 discloses the antibacterial agent linezolid as well as a process for its preparation. EXAMPLE 5 reports the linezolid produced had a mp of 181.5–182.5°.

There are many other disclosures of processes to prepare linezolid. *J. Med. Chem.*, 39(3), 673–9 (1996) reports the linezolid was, "recrystallized from ethyl acetate and hexanes . . . white crystals, m.p. 181.5–182.5C." It also sets forth the IR spectrum as "3284, 3092, 1753, 1728, 1649, 1565, 1519, 1447, 1435".

*Tetrahedron Lett.*, 40(26), 4855 (1999) discloses linezolid and a process to prepare linezolid. However, this document does not set forth the melting point or IR spectrum of the linezolid prepared.

U.S. Pat. No. 5,837,870 (International Publication WO97/37980 of PCT/US97/03458) discloses a process to prepare linezolid. Linezolid is described in EXAMPLE 18, which does not set forth the melting point or IR spectrum of the linezolid prepared.

International Publication WO99/24393 of PCT/US98/20934 discloses a process to prepare linezolid. Linezolid is described in EXAMPLES 8, 9 and 12 which do no set forth the melting point or IR spectrum of the linezolid prepared.

The form of linezolid being used in the clinical trials to support the filing of the NDA is Form II.

SUMMARY OF INVENTION

Disclosed is a (S)-N-[[3-[3-fluoro-4-(4-morpholinyl)phenyl]-2-oxo-5-oxazolidinyl]methyl]acetamide, crystal "Form II" with a powder X-ray diffraction spectrum of:

| d-Spacing (Å) | Two-Theta Angle (°) | Relative Intensity (%) |
| --- | --- | --- |
| 12.44 | 7.10 | 2 |
| 9.26 | 9.54 | 9 |
| 6.37 | 13.88 | 6 |
| 6.22 | 14.23 | 24 |
| 5.48 | 16.18 | 3 |
| 5.28 | 16.79 | 100 |
| 5.01 | 17.69 | 2 |
| 4.57 | 19.41 | 4 |
| 4.50 | 19.69 | 2 |
| 4.45 | 19.93 | 6 |
| 4.11 | 21.61 | 15 |
| 3.97 | 22.39 | 23 |
| 3.89 | 22.84 | 4 |
| 3.78 | 23.52 | 7 |
| 3.68 | 24.16 | 1 |
| 3.52 | 25.28 | 13 |
| 3.34 | 26.66 | 1 |
| 3.30 | 27.01 | 3 |
| 3.21 | 27.77 | 1 |

Also disclosed is (S)-N-[[3-[3-fluoro-4-(4-morpholinyl)phenyl]-2-oxo-5-oxazolidinyl]methyl]acetamide, crystal "Form II" with an infrared (IR) spectrum as a mineral oil mull: 3364, 1748, 1675, 1537, 1517, 1445, 1410, 1401, 1358, 1329, 1287, 1274, 1253, 1237, 1221, 1145, 1130, 1123, 1116, 1078, 1066, 1049, 907, 852 and 758 cm$^{-1}$.

Further disclosed is a process to prepare (S)-N-[[3-[3-fluoro-4-(4-morpholinyl)phenyl]-2-oxo-5-oxazolidinyl]methyl]acetamide, crystal "Form II " which comprises:

(1) producing (S)-N-[[3-[3-fluoro-4-(4-morpholinyl)phenyl]-2-oxo-5-oxazolidinyl]methyl]acetamide in greater than 98% enantiomeric purity, (2) mixing the greater than 98% enantiomerically pure (S)-N-[[3-[3-fluoro-4-(4-morpholinyl)phenyl]-2-oxo-5-oxazolidinyl]methyl]acetamide in a solvent or mixture of solvents at a temperature below a temperature of about 80° and (3) separating the (S)-N-[[3-[3-fluoro-4-(4-morpholinyl)phenyl]-2-oxo-5-oxazolidinyl]methyl]acetamide crystal "Form II" from the solvent(s).

DETAILED DESCRIPTION OF THE INVENTION

Linezolid, (S)-N-[[3-[3-fluoro-4-(4-morpholinyl)phenyl]-2-oxo-5-oxazolidinyl]methyl]acetamide, is a known pharmaceutically useful antibacterial agent, see U.S. Pat. No. 5,688,792 (EXAMPLE 5). Linezolid can be used orally or given by IV as a sterile solution.

When linezolid was originally produced, the crystal form was Form I. Form II differs from Form I in its IR spectrum, X-ray powder diffraction spectrum and melting point.

Once linezolid is synthesized, crystal Form II is prepared by starting with linezolid of high enantiomeric purity. It is preferred that the linezolid be more than 98% enantiomerically pure, it is more preferred that the linezolid be more than 99% pure and it is even more preferred that the linezolid be 99.5% pure. The linezolid of greater than 98% enantiomeric purity to be used to form crystal form II can either be in solution or be a solid. The linezolid starting material, solid or solution, is mixed with a solvent selected from the group consisting of:

water, acetonitrile, chloroform, methylene chloride, toluene, $R_1$—OH where $R_1$ is $C_1$–$C_6$ alkyl, $R_1$—CO—$R_2$ where $R_2$ is $C_1$–$C_6$ alkyl or phenyl substituted with 1 thru 3 $R_1$ where $R_1$ is as defined above, and where $R_1$ is as defined above, $R_1$—CO—O—$R_2$ where $R_1$ is $C_1$–$C_6$ alkyl and $R_1$ is as defined above, $R_1$—O—$R_2$ where $R_1$ is $C_1$–$C_6$ alkyl and $R_1$ is as defined above. It is preferred that the solvent be selected from the group consisting of water, ethyl acetate, methanol, ethanol, propanol, i-propanol, butanol, acetonitrile, acetone, methyl ethyl ketone, chloroform, methylene chloride, toluene, xylene, diethyl ether, or methyl-t-butyl ether. It is more preferred that the solvent be ethyl acetate, acetone, acetonitrile, propanol, or isopropanol. It is most preferred that the solvent be ethyl acetate.

The mixture of linezolid in the solvent is agitated at a temperature below 80° until crystals of Form II are formed and crystals of other solid forms, such as Form I, disappear. It is preferred to dissolve the linezolid in ethyl acetate at a temperature near the boiling point of the solvent. This mixture is cooled to a temperature of about 70°. The mixture may be seeded with crystals of Form II to facilitate crystallization. It is preferred that the solid product is cooled and agitated at a temperature between about 45° and about 60° until the solids consist only of Form II crystals. It is most preferred to maintain the slurry at a temperature of about 55°. It is preferred to mix the linezolid and solvent for at least 10 min, it is even more preferred to mix the linezolid and solvent for at least 20 min and it is most preferred to mix the linezolid and solvent for at least 30 min. The time and temperature will vary depending on the solvent selected. With ethyl acetate it is preferred to mix for not less that 60 minutes.

The crystalline slurry may be further cooled to improve yield, and the solid Form II product may be isolated. The mixture may be further cooled and agitated. Other measures which can be used to facilitate crystallization include, but are not limited to, cooling, concentration of the solution by evaporation or distillation, or through addition of other solvents.

The crystals are isolated by procedures known to those skilled in the art.

Crystal Form II is the most stable form below about 85°. It is preferred to use starting material with less than 0.2% of the R enantiomer of linezolid to minimize or eliminate the formation of a pseudoracemic solid solution of the two enantiomers which tends to crystallize as the Form I solid, even at temperatures below 85°.

It is well known to those skilled in the art that linezolid is useful as an antibacterial agent, see for example U.S. Pat. No. 5,688,792.

DEFINITIONS AND CONVENTIONS

The definitions and explanations below are for the terms as used throughout this entire document including both the specification and the claims.

DEFINITIONS

Linezolid refers to (S)-N-[[3-[3-fluoro-4-(4-morpholinyl) phenyl]-2-oxo-5-oxazolidinyl]methyl]acetamide the compound of formula:

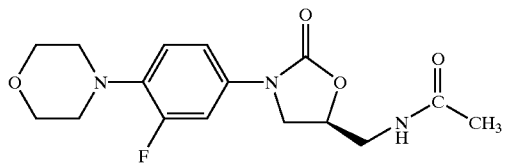

All temperatures are in degrees Centigrade.

IR refers to infrared spectroscopy.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

The term $C_1$–$C_6$ alkyl means alkyl of 1 thru 6 carbon atoms and isomers thereof where such exist.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Preparation of Crystal Form II of Linezolid

Linezolid with better than 99.8% enantiomeric purity, less than 0.2% of the R enantiomer, (1.99 grams) is mixed with ethyl acetate (100 mL). The flask is stoppered and heated to 65° with constant stirring in a temperature controlled oil bath. The linezolid is completely dissolved and the mixture is stirred for an additional 10 minutes. The temperature is maintained at 55° in the flask and one neck of the flask is unstoppered to allow slow evaporation of the solvent. A gentle stream of nitrogen is blown across the open neck to aid in evaporation. Solids spontaneously precipitated from solution and the volume is reduced by about 25% of the initial volume. The flask is sealed and mixed for 90 minutes while maintaining the mixture at 55°. The mixture was then cooled to about 23° while being stirred. The solids are isolated by vacuum filtration using a sintered glass funnel to give linezolid in crystal form. Analysis by powder X-ray diffraction indicates that the solids are linezolid crystal Form II.

What is claimed is:

1. (S)-N-[[3-[3-fluoro-4-(4-morpholinyl)phenyl]-2-oxo-5-oxazolidinyl]methyl] acetamide, crystal "Form II " with a powder X-ray diffraction spectrum of:

| d-Spacing (Å) | Two-Theta Angle (°) | Relative Intensity (%) |
|---|---|---|
| 12.44 | 7.10 | 2 |
| 9.26 | 9.54 | 9 |
| 6.37 | 13.88 | 6 |
| 6.22 | 14.23 | 24 |
| 5.48 | 16.18 | 3 |
| 5.28 | 16.79 | 100 |
| 5.01 | 17.69 | 2 |
| 4.57 | 19.41 | 4 |
| 4.50 | 19.69 | 2 |

| d-Spacing (Å) | Two-Theta Angle (°) | Relative Intensity (%) |
|---|---|---|
| 4.45 | 19.93 | 6 |
| 4.11 | 21.61 | 15 |
| 3.97 | 22.39 | 23 |
| 3.89 | 22.84 | 4 |
| 3.78 | 23.52 | 7 |
| 3.68 | 24.16 | 1 |
| 3.52 | 25.28 | 13 |
| 3.34 | 26.66 | 1 |
| 3.30 | 27.01 | 3 |
| 3.21 | 27.77 | 1. |

2. (S)-N-[[3-[3-fluoro-4-(4-morpholinyl)phenyl]-2-oxo-5-oxazolidinyl]methyl] acetamide, crystal "Form II" with an infrared (IR) spectrum as a mineral oil mull: 3364, 1748, 1675, 1537, 1517, 1445, 1410, 1401, 1358, 1329, 1287, 1274, 1253, 1237, 1221, 1145, 1130, 1123, 1116, 1078, 1066, 1049, 907, 852 and 758 $cm^{-1}$.

* * * * *